United States Patent
Fox et al.

(10) Patent No.: US 11,715,563 B1
(45) Date of Patent: Aug. 1, 2023

(54) SYSTEMS AND METHODS FOR EVALUATING LOCATION DATA

(71) Applicant: MASSACHUSETTS MUTUAL LIFE INSURANCE COMPANY, Springfield, MA (US)

(72) Inventors: Adam Fox, Springfield, MA (US); Sears Merritt, Groton, MA (US); Marc Maier, Springfield, MA (US)

(73) Assignee: Massachusetts Mutual Life Insurance Company, Springfield, MA (US)

(*) Notice: Subject to any disclaimer, the term of this patent is extended or adjusted under 35 U.S.C. 154(b) by 737 days.

(21) Appl. No.: 16/735,445

(22) Filed: Jan. 6, 2020

Related U.S. Application Data

(60) Provisional application No. 62/789,010, filed on Jan. 7, 2019.

(51) Int. Cl.
| | |
|---|---|
| *G16H 50/30* | (2018.01) |
| *G06N 20/00* | (2019.01) |
| *G06Q 40/08* | (2012.01) |
| *G16H 40/67* | (2018.01) |
| *H04W 4/33* | (2018.01) |
| *H04W 4/029* | (2018.01) |
| *G16H 10/60* | (2018.01) |
| *G06N 7/01* | (2023.01) |

(52) U.S. Cl.
CPC ............. *G16H 50/30* (2018.01); *G06N 7/01* (2023.01); *G06N 20/00* (2019.01); *G06Q 40/08* (2013.01); *G16H 10/60* (2018.01); *G16H 40/67* (2018.01); *H04W 4/029* (2018.02); *H04W 4/33* (2018.02)

(58) Field of Classification Search
None
See application file for complete search history.

(56) References Cited

U.S. PATENT DOCUMENTS

| | | | | |
|---|---|---|---|---|
| 5,337,750 | A * | 8/1994 | Walloch | A61B 5/02225 600/494 |
| 10,902,065 | B1* | 1/2021 | Merritt et al. | G06F 16/252 |
| 2005/0209785 | A1* | 9/2005 | Wells et al. | G16B 40/30 702/19 |
| 2006/0173663 | A1* | 8/2006 | Langheier et al. | G16H 50/20 703/11 |
| 2008/0133572 | A1* | 6/2008 | Verhey-Henke et al. | G16H 10/20 707/999.102 |

(Continued)

*Primary Examiner* — Robert A Sorey
(74) *Attorney, Agent, or Firm* — Foley & Lardner LLP

(57) ABSTRACT

Disclosed herein are embodiments of systems, methods, and products comprises an analytic server, which determines user health attributes by tracking the user's behaviors and activities within a predetermined space. The analytic server receives tracking data from a set of sensors installed in the predetermined space. The sensors track a beacon worn by the user. The analytic server determines micro-locations and user behaviors based on the tracking data. The analytic server determines the coordinates of the sensors based on the sensor identifiers and maps the coordinates to regions by referring to a floor plan map. The analytic server determines the user behaviors and activities by aggregating the micro-locations and regions the user visited at different time. The analytic server determines the user's health score based on the micro-locations and user behaviors by executing an artificial intelligence model. The analytic server determines a recommendation of premium based on the health score.

20 Claims, 5 Drawing Sheets

(56) References Cited

U.S. PATENT DOCUMENTS

| | | | | |
|---|---|---|---|---|
| 2008/0171919 | A1* | 7/2008 | Stivoric et al. | A61B 5/318 600/301 |
| 2008/0319802 | A1* | 12/2008 | Abraham et al. | G06Q 40/08 705/4 |
| 2011/0161100 | A1* | 6/2011 | Peak et al. | G01C 21/36 705/2 |
| 2017/0286622 | A1* | 10/2017 | Cox et al. | G16H 50/30 |
| 2020/0174517 | A1* | 6/2020 | Martinez et al. | G16H 80/00 |
| 2020/0193489 | A1* | 6/2020 | Rabinowitz et al. | G06N 20/00 |

* cited by examiner

SYSTEMS AND METHODS FOR EVALUATING LOCATION DATA

CROSS REFERENCE TO RELATED APPLICATIONS

The application claims priority to U.S. Provisional Pat. Application No. 62/789,010, filed Jan. 7, 2019, which is incorporated herein in its entirety.

TECHNICAL FIELD

The present disclosure relates in general to micro-location data transmission and analytics.

BACKGROUND

Many health-related consumer protection companies may require health information from consumers for underwriting. Traditionally, the customers may be presented an initial questionnaire, which typically asks general questions related to age, weight, medical history, and the like. However, the customers may need to undergo medical examinations, which typically involve collecting body fluids and different physical measurements. However, collecting such data is often a problem for the customers for a variety of physical and/or psychological reasons and is often a major barrier to health-related customer protection companies and institutions attempting to enroll new customers. More particularly, the consumers often do not want to have blood drawn for fear of needles, do not want to undergo medical screening, do not have the time, and many other reasons.

The problems associated with transfer and pooling of risk are integral elements in the operation of life insurance systems. By grouping individuals' risk, the insurance systems are able to cover losses based on possibly future arising risks, out of a common pool of resources captured by the insurance systems. However, in order to maintain some degree of equity among individuals exhibiting different mortality risks, the insurance systems must capture, assess and classify risk of applicants for life insurance according to appropriate criteria or risk factors. While traditional underwriting practice has been to require applicants for life insurance to undergo medical examinations, including collection of body fluids and various physical measurements and analysis of risk factors based on these inputs; in the present disclosure such risk factors are sometimes called but this can be a barrier to enrolling new customers for reasons previously mentioned. What is needed is improve methods for predictive modeling of mortality for applicants for financial products such as life insurance.

SUMMARY

While the traditional medical examinations may be inconvenient and time consuming, the increasingly pervasive passive sensors may provide a new way to estimate customer risk and improve the overall user experience. The sensors may be deployed in a building or office space and generate micro-location data for the customers/users. The micro-location data may replace the lab data on body fluids (e.g., blood sample, urine sample). The micro-location may provide valuable information on a user's health status.

For the aforementioned reasons, there is a desire for a more efficient system and method for evaluating customer health and risk by collecting and analyzing micro-location data of the users. Discussed herein are systems and methods for collecting micro-location data from sensors over a period, training an artificial intelligence model on historical data, determining a health score based on the micro-location data using the artificial intelligence model, and determining a recommendation of products or a premium based on the health score.

In an embodiment, a method comprises periodically monitoring, by a server, location information of a plurality of users by periodically receiving, from an application executing on a mobile device of each user, location signals emitted by a plurality of beacons; continuously updating, by the server, a user activity profile for each user containing a movement pattern representative of the user and based on the location information monitored via the plurality of beacons, a distance traveled within a predetermined time period, and a time spent at a pre-determined location; generating, by the server, an activity score for each user based on the movement pattern in each user's activity profile; executing, by the server, an artificial intelligence model to determine a health score associated with each user, the artificial intelligence model is trained based on historical data associated with a set of at least one of existing and past users, wherein the artificial intelligence model is configured to, upon receiving a user's activity score, determine an estimated health score of that user; when the health score satisfies a threshold, determine, by the server using a predetermined pricing algorithm, a premium for each user based on each user's health score; and when the health score does not satisfy a threshold, routing the user's activity profile to an electronic device.

In another embodiment, a method comprises monitoring, by a server, location information of a plurality of users, using location signals received from a plurality of sensors, wherein each of the plurality of sensors is configured to receive signals from a beacon when the beacon is within a predetermined distance from the sensor, wherein the beacon is configured to attach to each user and constantly transmit a signal; continuously generating, by the server, a user activity profile for each user containing a movement pattern representative of the user and based on the location information monitored via the plurality of beacons, a distance traveled within a predetermined time period, and a time spent at a pre-determined location; generating, by the server, an activity score for each user based on the movement pattern in each user's activity profile; executing, by the server, an artificial intelligence model to determine a health score associated with the user, the artificial intelligence model is trained based on historical data associated with a set of existing or past users, wherein the artificial intelligence model is configured to, upon receiving a user's activity score, determine an estimated health score of that user; when the health score satisfies a threshold, determining, by the server using a predetermined pricing algorithm, a premium for each user based on each user's health score; and when the health score does not satisfy a threshold, routing the user's activity profile to an electronic device.

It is to be understood that both the foregoing general description and the following detailed description are exemplary and explanatory and are intended to provide further explanation of the invention as claimed.

BRIEF DESCRIPTION OF THE DRAWINGS

The present disclosure can be better understood by referring to the following figures. The components in the figures are not necessarily to scale, emphasis instead being placed upon illustrating the principles of the disclosure. In the fig

DETAILED DESCRIPTION

Figure 1A:
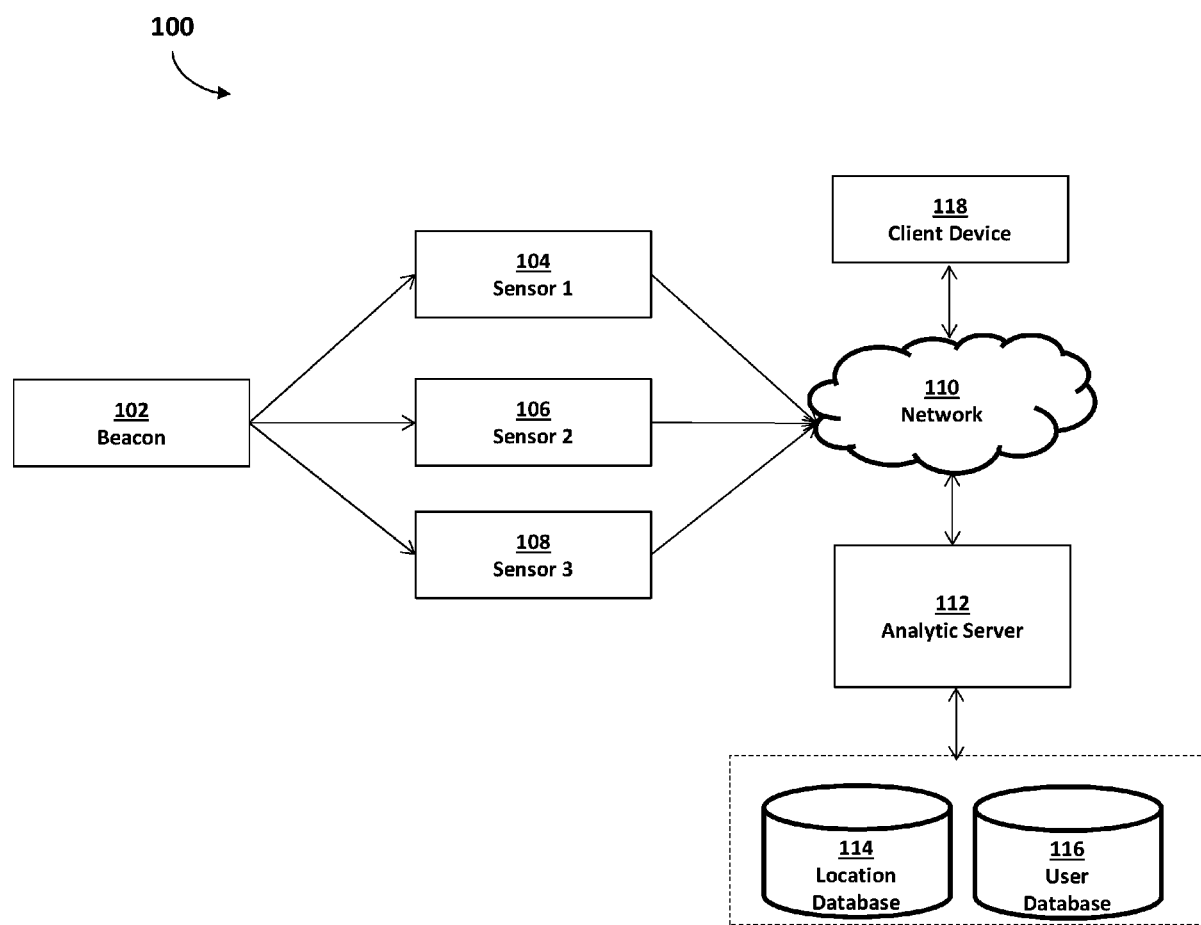
- FIG. 1A illustrates a computer system for evaluating micro-location data, according to an embodiment.

Reference will now be made to the illustrative embodiments illustrated in the drawings, and specific language will be used here to describe the same. It will nevertheless be understood that no limitation of the scope of the claims or this disclosure is thereby intended. Alterations and further modifications of the inventive features illustrated herein, and additional applications of the principles of the subject matter illustrated herein, which would occur to one ordinarily skilled in the relevant art and having possession of this disclosure, are to be considered within the scope of the subject matter disclosed herein. The present disclosure is here described in detail with reference to embodiments illustrated in the drawings, which form a part here. Other embodiments may be used and/or other changes may be made without departing from the spirit or scope of the present disclosure. The illustrative embodiments described in the detailed description are not meant to be limiting of the subject matter presented here.

FIG. 1A illustrates components of a system 100 for evaluating micro-location data, according to an embodiment. Micro-location data represents data used to describe a virtual fenced location defined by indoor positioning systems. The boundaries of a micro-location can be set by a user or by an administrator of the system.

An indoor positioning system is a system that attempts to provide an accurate position of a computing device inside of a covered structure. In addition to using location information from a beacon, certain embodiments can use triangulation to assess more accurately the location of a receiving device. For instance, the receiving device may receive signals from more than one source or of more than one type, e.g., Wi-Fi, BLE, and GPS. By relying on more than once source, the reliability and accuracy of the systems and methods disclosed herein are enhanced.

The system 100 may comprise an analytic server 112 with a location database 114 and a user database 116, a set of sensors 104, 106, 108, an electronic client device 118, that are connected with each other via hardware and software components of one or more networks 110. In addition, the set of sensors 104, 106, and 108 may receive signals from a beacon 102 coupled to a user and track the locations of the user.

A beacon is a device configured to transmit a data packet, which is used by a receiving device to identify the transmitting device and compute the relative distance between the transmitting device and the receiving device. Beacons can be physical devices or virtual beacons. Beacons transmit small packets of data. Currently, beacons repeatedly transmit data packets in set intervals. There are several types of beacons and associated protocols available in the market such as iBeacon system (implemented by Apple®), AltBeacon (provided by Radius Networks), and EddyStone® (from Google®). The iBeacons and AltBeacons broadcast a data packet consisting mainly of following pieces of information —a Universally Unique Identifier (UUID), a major number, a minor number, and a transmission power level known as the "Broadcasting Power." These formats require external databases to give meaning to the beacon data packets. Receiving devices can approximate distance from the beacon by comparing the Broadcasting Power to the strength of the signal as received, known as the Received Signal Strength Indicator (RSSI). As these devices typically transmit that packet over and over again, this type of transmission defines the advertising functionality of beacons. Beacons supporting the Eddystone format broadcast three different packets: a unique ID number, a URL address, and telemetries based on sensors. They do not require an external database; instead they use web links to either link to data directly and could function via a two-way communication method. The Eddystone-URL frame type broadcasts information that can be used by a phone even without a specialized application. Virtual beacons may not require specialized devices and may use existing indoor positioning systems and the user devices to deliver location-based information. Beacons can be configured to broadcast sensor data such as temperature and battery level, or even data gathered from other sensors in the room such as motion-detectors.

Examples of the network 110 include, but are not limited to, Local Area Network (LAN), Wireless Local Area Network (WLAN), Metropolitan Area Network (MAN), Wide Area Network (WAN), and the Internet. The communication over the network 110 may be performed in accordance with various communication protocols, such as Transmission Control Protocol and Internet Protocol (TCP/IP), User Datagram Protocol (UDP), and IEEE communication protocols.

The sensors 104, 106, 108 may be any location-aware computing devices that can detect events or changes in its environment and send the detected information to the analytic server 112. Location-aware devices are computing devices that can passively or actively determine their location. Location signal data can be accessed and passed to the computing device in different ways. Location signals that can be detected by location-aware devices can be outdoor signals, indoor signals, or combinations thereof. Outdoor signals can be GPS, Wi-Fi, IP address, cell-tower triangulation, and user-reported location. Indoor signals can be A-GPS, indoor positioning system (IPS), and Wi-Fi triangulation.

For example, the sensors 104, 106, 108 may receive a wireless signal from one or more beacons 102 when the beacons are within a predetermined distance from the sensors. When a sensor receives a signal, it may identify the identifier of the beacon and the distance between the sensor and the beacon. The figure shows only a limited number of sensors 104, 106, 108, it should be appreciated that more sensors may be communicatively coupled to one another, over a wire and/or wireless network of sensors. Locations, such as office building, schools, campuses, governmental or administrative buildings, and the like, may implement localized networks of sensors to transmit and/or collect micro-location data. The sensors 104, 106, 108 can be placed strategically indoors or outdoors to perform many actions. The identifiers of the sensors may be programmed and associated with particular locations where they are installed. The sensors 104, 106, 108 may track the activities of a user by tracking the locations of the beacon coupled to the user. Specifically, when the user moves within the building, the sensors along the user's path may receive the signals omitted from the beacon coupled to the user. In other words, the sensors within a certain range of the beacon may sense the existence of the beacon and therefore determine the location of the user wearing the beacon.

The beacon 102 may be any small, battery-powered physical device that sends out a low-voltage signal, such as Bluetooth Low-Energy (BLE), for a programmable distance between about a few centimeters to a few meters. The frequency of sending the signal can also be programmable; for example, a signal can be sent every 100-400 milliseconds. The beacon may be transmitting small data packets repeatedly in set intervals. A data packet can be the same as defined in the Bluetooth specification or any other data packet that transmits a unique identifier of the beacon. The sensors 104, 106, 108 may be able to sense the signals or receive the data packets transmitted by the beacon when the beacon is within a predetermined distance from the sensors. The beacon 102 may be a small and unobtrusive device coupled/attached to the user (e.g., worn by the user) as the user is within the building or office space. For example, the users may wear beacon around their neck as a pendant. The beacon identifier (ID) is corresponding to the user identifier. For example, the user database may include a record that identifies the user ID and the corresponding beacon ID. As a result, the beacon location is the user location. The sensors 104, 106, 108 may be able to track the user's location by tracking the beacon.

The analytic server 112 may be any computing device comprising a processor and other computing hardware and software components, configured to evaluate user health based on micro-location data. The analytic server 112 may be logically and physically organized within the same or different devices or structures, and may be distributed across any number of physical structures and locations (e.g., cabinets, rooms, buildings, cities). The analytic server 112 may receive micro-location data of the beacon 102 from the sensors 104, 106, 108. The micro-location data may include the identifiers of the sensors detecting the signals of the beacon, and the detected beacon identifier. As discussed above, the identifiers of the sensors may be programmed and associated with particular locations (e.g., X, Y, Z coordinates) where they are installed. Such association information and a floor plan map of the building or office space may be stored in the location database 114. The analytic server 112 may access the location database 114 to identify the location coordinates of the sensors and determine the region (e.g., standing desk, restroom, kitchen, conference room, and the like) correlated with the coordinates based on the sensor identifiers. Furthermore, the analytic server 112 may determine the user identifier corresponding to the tracked beacon identifier by accessing the user database 116, and determine the user's location and activity based on the tracking of the user's beacon.

In addition, the analytic server 112 may train an artificial intelligence model based on historical data of existing users. The artificial intelligence model may build a correlation between the micro-locations and the health status by training of the historical data. Specifically, the micro-locations of a user may reflect the user's lifestyle or activities, which may be further related with the user's health status and risk. The artificial intelligence model may utilize such a correlation to predict the user's health status based on the user's micro-locations. As a result, the micro-location data may replace the medical examination data that are typically measured by collecting body fluid (e.g., blood, urine, etc.) at a medical examination. Furthermore, the analytic server 112 may determine a health score and a recommendation of products or a premium based on the health score.

The location database 114 may be any non-transitory machine-readable media configured to store data, including the floor plan map of the building and the distribution of the sensors within the building, such as the identifiers of the sensors 104, 106, 108, the sensor's coordinates, micro-location, and the corresponding region in the building. The micro-location may be locations identified with a level of precision within a building or room. The location database 114 may also include other related data that may be used to better understand the user's activity.

The user database 116 may be any non-transitory machine-readable media configured to store data, including the user identifier, the corresponding beacon identifier, the paths or locations of the user determined based on the tracking data from the sensors. In addition, the user database 116 may include the user profile or attributes, activity profile, health attributes, health score, premium, different products, the correlation between the health score and the premium, and the like associated with the user. The user database 116 may include other related data that may be used to better evaluate the user's micro-location data.

The electronic client device 118 may be any computing device allowing a user to interact with the analytic server 112 via the network 110. The electronic client device 118 may be any computing device comprising a processor and non-transitory machine-readable storage medium. The examples of the electronic client device 118 may include, but are not limited to, a desktop computer, a laptop, a personal digital assistant (PDA), a smartphone, a tablet computer, and the like. The electronic client device 118 may comprise any number of input and output devices supporting various types of data, such as text, image, audio, video, and the like. The analytic server 112 may collect user attributes and profile data during the registration of the user and record the user data by updating the user database 116. For example, the analytic server may require the user to provide user attributes including age, sex, height, weight, and the like. During the registration process, the analytic server 112 may display a graphical user interface (GUI) on the electronic client device 118 and receive the user's input when the user interacts with the graphical user interface. The analytic server may create a user profile in the user database 116 based on the user input. In some embodiments, the analytic server may web crawl various websites (e.g., health-related networks, social networks, and the like) and collect relevant data of the user from various websites.

Figure 1B:
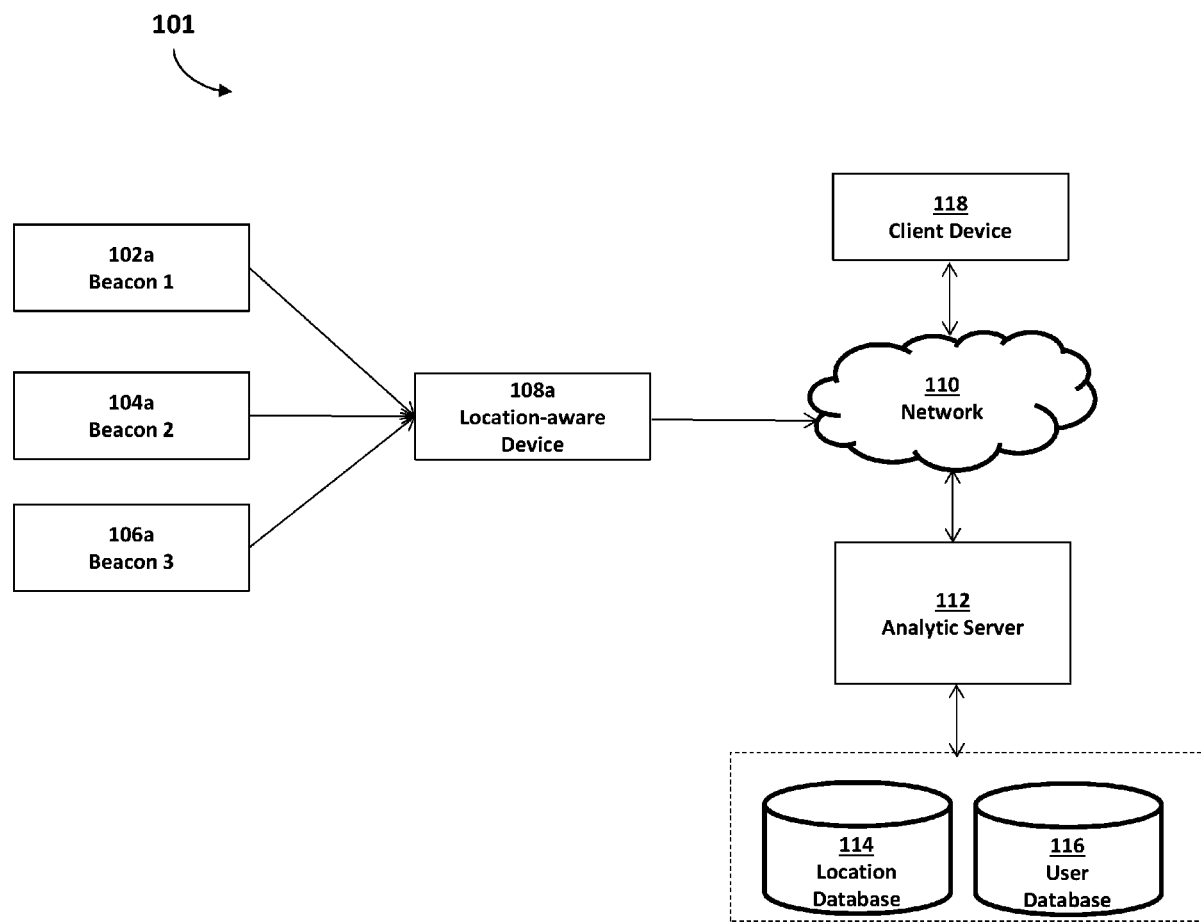
FIG. 1B illustrates an alternative computer system for evaluating micro-location data, according to an embodiment.

FIG. 1B illustrates components of an alternative system 101 for evaluating micro-location data, according to an embodiment. The alternative system may provide a different way for collecting the micro-location data. In this alternative system, a plurality of beacons 102a, 104a, and 106a transmit a plurality of location signals that are received by a location-aware device 108a. The device 108a then transmits a device identifier and the plurality of location signals from the plurality of beacons 102a, 104a, and 106a via the network 110 to one or more servers constituting the analytic server 112. The device identifier can be a distinctive combination of numbers or characters associated with a particular computing device for the purpose of uniquely identifying that computing device to other devices and systems that are communicatively coupled to it. The system includes the location database 114 and the user database 116.

In some embodiments, the UUIDs or unique identifiers of the beacons 102a, 104a, and 106a must be programmed and associated with particular locations where they are installed. The beacons 102a, 104a, 106a continuously broadcast information, for example in the form of data strings, at a pre-determined interval, like a heartbeat of data broadcasts, which are then captured by one or more applications on the location-aware devices 108a. The data fields in these broadcasted data strings could include an identifier of an individual beacon, location of the beacon in the office space, time of day, and any information designed for consumption by the location-aware devices.

The location-aware device 108a can be any mobile computing devices, e.g., smartphone or tablets, which can receive a wireless signal from one or more transmitters of location signals. When the location-aware device 108a receives the location signals, it can process it using one or more mobile applications in communication with one or more servers constituting the analytic server 112. Mobile applications of the micro-location evaluation system can be implemented as software that can be downloaded and installed on the location-aware device 108a. Examples of mobile application are GUI applications that may be available at, downloaded, and installed from a public software app stores or digital application distribution platforms, such as Apple iTunes®, Google play® Store and Amazon.com®, among others.

Beacons 102a, 104a, 106a may be any computing or other electronic device comprising a processor and a wireless interface capable of transmitting signals to a receiving device. The signals may contain binary data, and the binary data may represent various types of data and/or information for the location-aware device 108a to consume and implement. The components of the location-aware device 108a receiving the signals, may translate the signals into useful binary data triggering various tasks and process according to the application executed by the location-aware device 108a. The beacons 102a, 104a, 106a may implement any suitable components for wirelessly communicating with the location-aware device 108a, or other receivers. The technological components may include wireless networking hardware and the related protocols, such as a Bluetooth low energy (BLE) interface chip and the Bluetooth wireless communication protocols.

Although FIG. 1B shows only a limited number of beacons 102a, 104a, and 106a, it should be appreciated that more transmitters may be communicatively coupled to one another, over a wired and/or wireless network of transmitters. That is, locations, such as brick-and-mortar office buildings, schools, campuses of multiple buildings, governmental or administrative buildings, and the like, may implement localized networks of beacons to transmit and/or collect data, across a broader area. Furthermore, although the exemplary system described in FIG. 1B describes stationary beacons 102a, 104a, 106a, it should also be appreciated that beacons 102a, 104a, 106a may be any suitable stationary or mobile devices that are capable of performing the various tasks and processes described herein. Thus, a collection of beacons 102a, 104a, 106a can comprise a combination of mobile and stationary devices. It should also be appreciated that, although FIG. 1B describes beacons 102a, 104a, 106a performing one-way signal transmissions, beacons 102a, 104a, 106a may be capable of two-way communications (i.e., collecting data from signals transmitted by receiving devices), and may be capable of a number of functions or execute a variety of software modules. Non-limiting examples of beacons 102a, 104a, and 106a may include an iBeacon, AltBeacon, and EddyStone, a wireless router, a cellular phone, a tablet, a workstation, or any other suitable computing or other electronic device. The data strings from the beacon can comprise both constant identifiers that do not change with every broadcast and dynamic identifiers that change with every broadcast.

The analytic server 112 may receive location information from the location-aware device 108a, such as the user's mobile device (e.g., a smart phone) via an application executing on the mobile device. The location information may comprise the location signals emitted by the beacons 102a, 104a, 106a and received by the location-aware device 108a. As discussed above, based on the location information, the analytic server 112 may determine the activity and life style of the user.

Figure 2:
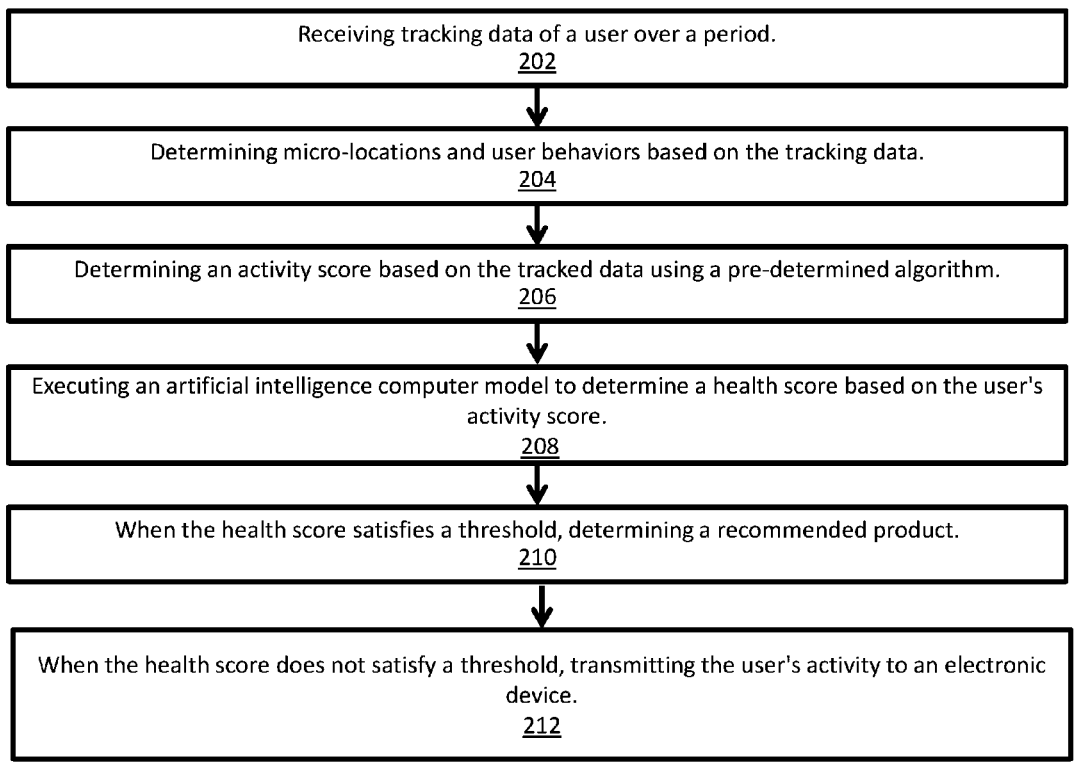
FIG. 2 illustrates a flowchart depicting operational steps for underwriting based on evaluation of micro-location data, according to an embodiment.

FIG. 2 illustrates execution of an exemplary method 200 for underwriting based on evaluation of micro-location data, according to an embodiment. Other embodiments may comprise additional or alternative steps, or may omit some steps altogether.

At step 202, the analytic server may receive tracking data collected by the sensors over a period. The sensors may be continuously monitoring the user behavior/activity in a pre-determined space (e.g., office space) by tracking the beacon worn by the user over a period. In operation, the sensors may receive signal from the beacon of a user when the user is within close proximity of the sensors. The received signal may include the beacon identifier that corresponds to user identifier. The sensors may report the tracking data comprising the beacon identifier, the timestamp. In addition, each sensor may include its own identifier in the report. The analytic server may receive tracking data comprising the triggered sensor identifier, the sensed beacon identifier, and the timestamp. The tracking data report may be in a JavaScript Object Notation (JSON) format.

The sensors may report the tracking data periodically (e.g., on a daily basis). In some embodiments, the analytic server may generate and transmit command instructions to the sensors to alter data collection setting. These command instructions may alter the frequency of data collection, the speed/frequency in which the information is communicated from the sensors, the period (e.g., start time, stop time) for data collection. For example, the analytic server may transmit a command instruction that changes the frequency of data reporting from once a day to once an hour.

In an alternative embodiment, the analytic server may monitor location information of a user using location signals received from the plurality of beacons. Specifically, the plurality of beacons may transmit a plurality of location signals to the location-aware device associated with the user. The user device may transmit a device identifier and the plurality of location signals from the plurality of beacons via a network to the analytic server.

At step 204, the analytic server may determine micro-locations and user behaviors based on the tracking data. Based on the sensor identifier, the analytic server may determine the micro-location of the sensor by mapping the sensor identifier to the corresponding coordinates. As a result, the analytic server may determine the micro-location of the user who is within the proximity of the sensor. Furthermore, the analytic server may determine the region (e.g., standing desk, restroom, kitchen, conference room, and the like) of the coordinates by referring to the floor plan map. For example, the analytic server may determine that the user is in the kitchen at 9:00 am. By aggregating the micro-locations of the user at different time indicated by timestamps, the analytic server may determine the behaviors, activities and lifestyle of the user. For example, the analytic server may also determine that the user goes to kitchen 10 times a day.

In an alternative embodiment, the analytic server may map the location signals received from the plurality of beacons to the corresponding coordinates, and determine the micro-location of the user. As discussed above, the data fields in broadcasted data strings from each of the plurality of beacons could include an identifier of an individual beacon, location of the beacon in the office space, time of day, and any information designed for consumption by the location-aware devices. The analytic server may integrate location signals received from beacons and other indoor positioning systems for better tracking the user's locations.

The floor plan map may include scale and coordinates data. The coordinates and corresponding region data of the floor plan map are stored in the location database. The analytic server may update the location database when there are any changes (e.g., moving furniture) with the floor plan and layout plan. For example, when a standing desk is moved to coordinates (X1, Y1, Z1), the analytic server may update the location database to make sure that coordinates (X1, Y1, Z1) corresponds to the standing desk.

The analytic server may create and update a user activity profile for each user based on the micro-locations monitored. The user activity profile may comprise data indicating a movement patterns, distance traveled within a predetermined time period, and time spent at a pre-determined location, which may further indicate the user's behaviors, activities and lifestyle.

At step 206, the analytic server may determine an activity score based on the tracked data using a pre-determined algorithm. The analytic server may apply the predetermined algorithm to the user's location data tracked using the methods and systems described above to determine an activity score for the user. As described above, the user's activity profile may include information, such as number of steps taken, number of active minutes, distance traveled, number of minutes spent in office, number of minutes standing, number of minutes spent at the gym, number of minutes spent in the kitchen, and the like. The analytic server may generate an activity score based on the above-mentioned factors and values. The activity score may represent a numerical value of the user's activities (within a predetermined period of time). To calculate the activity score, the analytic server may use a predetermined algorithm that accounts for different attributes within the user's activity profile. In some configurations, the predetermined algorithm may assign different weights to different attributes. For instance, the number of steps per day may be weighted higher than the number of minutes standing. As a result, the activity score may be a single score that summarizes the user's activities.

At step 208, the analytic server may execute an artificial intelligence computer model (AI model) to determine a health score based on the user's activity score. The analytic server may build the AI model to determine a health score (e.g., a health status, a health risk) for the user based on the user's activities generated from the micro-location data. More specifically, the analytic server may build the AI model by using the user's activity profile data as input. The user's activity profile data may include both activity data derived based on medical expertise (e.g., number of steps or distance walked, number of trips to water station, and the like) and activity data generated solely by analyzing the micro-location data (e.g., trends that are highly correlated to good or poor health). In addition, the analytic server may build the AI model by using any known demographic or health information of the user as input, including the user's age, sex, smoker status, answers to application questions, and the like. The AI model may comprise a survival random forest algorithm. The analytic server may also enrich the input of the AI model with public record data. The analytic server may execute the AI model with all the inputs to determine the health score, which may further determine the premium price, risk class and/or eligibility of the user for a certain product.

The AI model may utilize one or more artificial neural networks to generate a health score. The AI model may also use the health score and other monitored data to train itself (e.g., the analytic server may train the AI model). A neural network may include an interconnected group of artificial neurons where each neuron may represent a user attribute. For example, each neuron may represent one attribute associated with an existing or previous user in a database (e.g., stored within the user profile in database 116). The AI model may also comprise a mathematical or computational model comprising mathematical functions describing the relationship between each neuron within the neural network using "weight" and 'bias" factors. Furthermore, the AI model may also comprise a mathematical function describing how the neurons are divided into one or more layers (e.g., decision trees). The neural networks may be constructed using existing/past users' historical data. The historical data of existing/past users may comprise the users' micro-location data and health attributes (e.g., blood pressure, cholesterol, family history of diseases, heart condition, smoking status, diabetes, and any other dynamic biometric measurement or combination thereof). In addition, the historical data may comprise user attributes including age, sex, height, weight, and the like.

Based on the AI model, the analytic server may learn the hidden patterns in the historical data and identify a correlation between the micro-location data and the health attributes. Specifically, the micro-locations of a user may reflect the user's lifestyle or behaviors, which may be further related with the user's fitness, health status, and risk. For example, the fact that a user visits the kitchen 10 times a day may be an indication of obesity. The AI model may utilize such a correlation to predict the user's health status based on the user's micro-locations.

By executing the AI model generated based on historical data and existing/past users, the analytic server may predict a health score for the user. The AI model is particularly useful in inferring health score because the complexity and the volume of the data make manual calculations impractical, inefficient, and time-consuming. Furthermore, the AI model is also useful and beneficial because the analytic server may only need minimal user data (e.g., activity score) to achieve a numerical representation of the user's health. Moreover, by replacing the medical examination data, the micro-location data may provide a faster, less intrusive way for user health evaluation, thus improve user experience.

In some embodiments, the micro-location data may replace the medical examination data and biometric parameters that are typically measured by collecting body fluid (e.g., blood, urine, etc.) at a medical examination. For example, the analytic server may estimate the user's health attributes based on the user's activity profile (e.g., data indicating a number of bathroom visits, how long the user is working at a standing desk, a number of coffee breaks, or any other micro-location and behavior data). Furthermore, the analytic server may estimate the user's health/mortality risk based on the user's activity profile data. In some embodiments, the analytic server may also consider the user attributes (e.g., age, weight, gender, and the like) in the above-mentioned calculations.

Even though aspects of the present disclosure have been described as utilizing artificial intelligence, in some embodiments, the analytic server may use other algorithms that do not involve artificial intelligence. For instance, the analytic server may execute one or more predetermined rules to identify the health score based on the activity score.

At step 210, when the health score satisfies a threshold, the analytic server may determine a premium for the user based on the user's health score. The analytic server may determine the premium using a predetermined pricing algorithm. The analytic server may derive the correlation between the health score and the recommended premium based on historical user data. In some embodiments, the analytic server may utilize an AI model derive the correlation or identify a recommended premium. After deriving the correlation, the analytic server may use the correlation to determine a recommendation of a premium based on the health score. For example, for a new user in good health (e.g., health score satisfying a threshold), the analytic server may recommend a lower premium for a health insurance product. In some embodiments, the analytic server may recommend a group insurance premium for a group of users in the same workplace based on the group members' health score. In operation, the correlation between the score and the recommended premium may be stored in the user database. The analytic server may retrieve the database to determine a premium for a user based on the user's score.

At step 212, when the health score does not satisfy a threshold, the analytic server may rout (e.g., transmit) the user's data (e.g., activity profile, micro location data, activity score, health score) to a computing device of an agent (not shown). In some embodiments, more data (e.g., biometric data) may be needed to identify a suitable premium for the user (e.g., when the health score of a user is below a predetermined threshold). In those embodiments, the analytic server may notify a computing device of an agent where the agent is able to communicate with the user and gather more data to identify a suitable premium for the user.

In some configurations, the analytic server may periodically monitor the user's health related data (e.g., activity score and/or health score). The analytic server may also periodically update the user's activity score, health score, and/or recommended premium. The monitored data may also be used to train the AI model. As the analytic server encounters new and updated activity scores or health scores for a particular user, the analytic server may train the AI model accordingly. For instance, when encountered an updated score that deviates from the AI model's initial assessment, the AI model may reconfigure itself to adapt. This "learning" may lead to a more accurate determination of health score for future users.

In a non-limiting example, the analytic server determines a health score for a particular user to be a high value (e.g., healthy user). The analytic server may continue to monitor the user's activities for a predetermined time period and determine an updated health score that is inconsistent with the previously determined health score. Additionally or alternatively, the analytic server may also receive new data (e.g., biometric data) indicating that the user's actual health score deviates from the previously determined health score. As a result, the analytic server may use a back-propagation method to reconfigure the above-mentioned mathematical functions used in the AI model (e.g., weight and bias factors) and revise the AI model to account for the error. Therefore, in some configurations, the AI model is never complete and may be iteratively trained each time an erroneous health score is identified.

Figure 3:
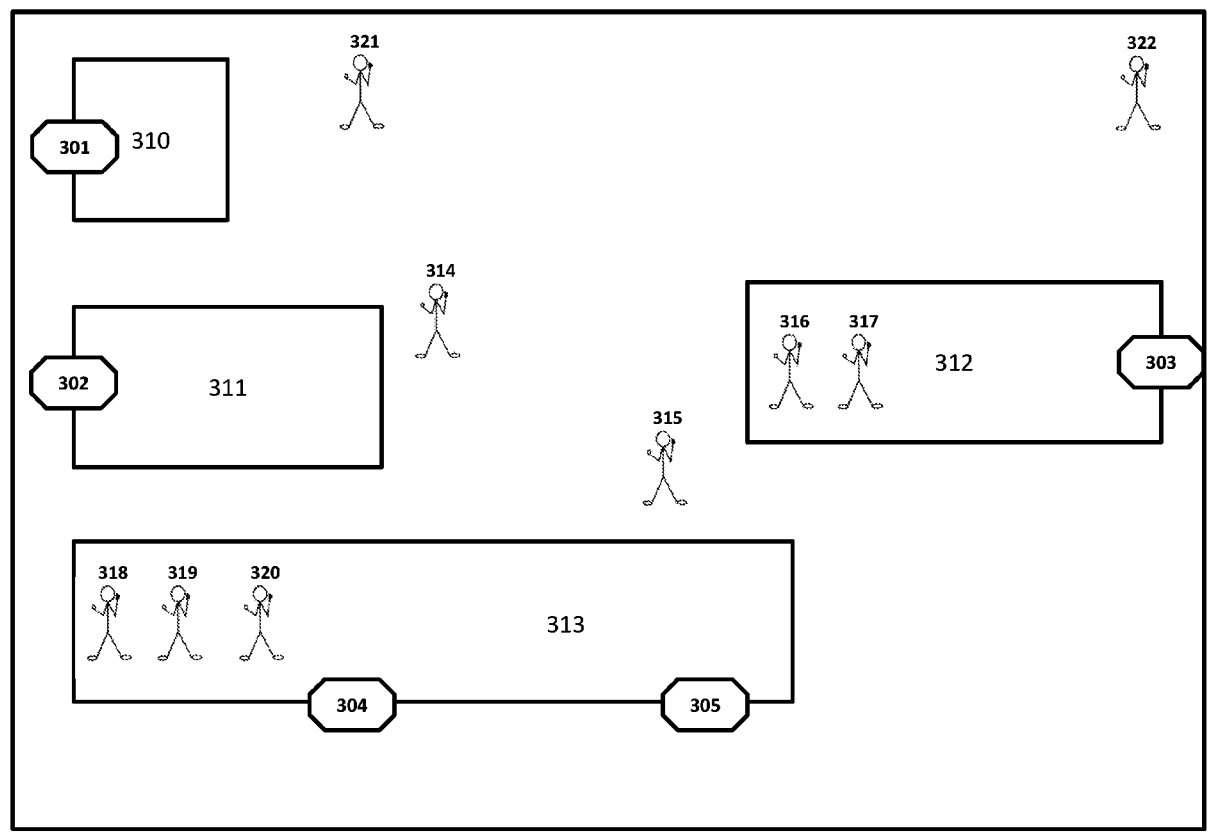
FIG. 3 illustrates a block diagram of various components of the alternative computer system in accordance with an embodiment.

FIG. 3 is a block diagram of various components of the alternative computer system in accordance with an embodiment. In an embodiment, as shown in FIG. 3, beacons are placed in specific areas of indoor space, such as conference rooms, hallways, kitchens, offices, and other areas in a workspace. Here, each one of the rooms 310, 311, and 312 has a beacon 301, 302, 303 associated with it, while room 313 has two beacons 304 and 305 associated with it. Each beacon can be configured such that the location signal range encompasses approximately the boundaries of the room. For example, beacon 301 associated with room 310 can have a 3 ft location signal range, beacon 302 associated with room 311 can have a 10 ft location signal range, and beacon 303 associated with room 312 can have a 20 ft. location signal range. Beacons 304 and 305 associated with room 313 can be short-range transmission beacons instead of long-range beacons, in order to avoid across-the-wall transmission issues. When a location-aware device 314 is within the location signal range of any one of the beacons, such as beacon 302 associated with room 311, then a receiver in the location-aware device 314 detects the location signals from beacon 302 and communicates them to an application program. For example, beacon 302 broadcasts the following data packet UUID 109 876 543 210 23 Major: 31 Minor: 4. The location-aware device 314 receives this data packet and determines that it is from beacon 302 situated in room 311 on a certain floor in a specific building of company X, and transmits this information along with a device identifier or a user identifier associated with the location-aware device 314 to the analytic server via the application program.

As another example, when a location-aware device 315 is within the location signal range of any one of the beacons, such as beacon 303 associated with room 312 and beacon 305 associated with room 313, then a receiver in the location-aware device 315 detects the location information (e.g., signals received from beacons 303 and 305) and communicates them to an application program. For example, beacon 303 broadcasts the following data packet UUID 129 866 553 220 23 Major: 30 Minor: 6, while beacon 305 broadcasts the following data packet UUID 199 866 533 200 22 Major: 35 Minor: 8. The location-aware device 315 receives these two data packets and determines that they are from beacons 303 and 305 situated in room 312 and 313 on a certain floor in a specific building of company X, and transmits this information along with a device identifier or a user identifier associated with the location-aware device 315 to the analytic server via the application program.

Figure 4:
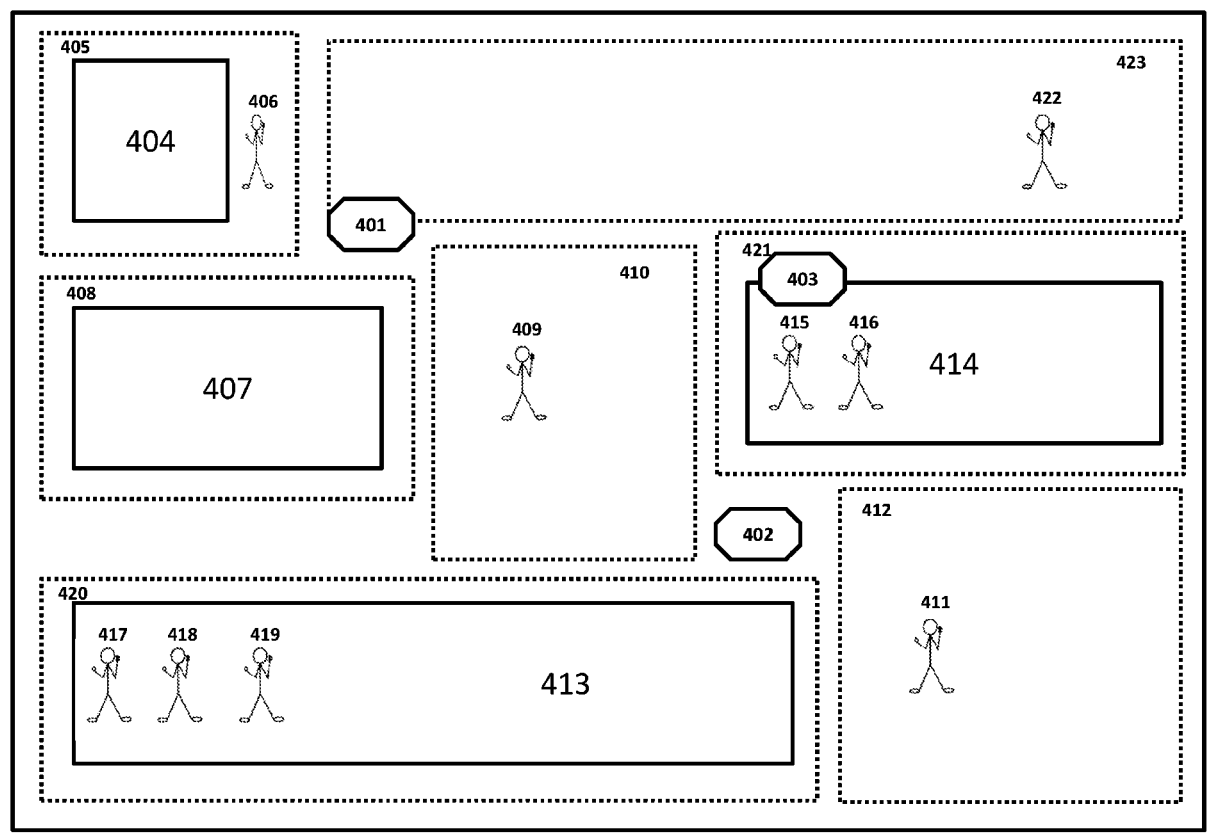
FIG. 4 illustrates a block diagram of various components of the alternative computer system in accordance with another embodiment.

FIG. 4 is a block diagram of various components of the alternative computer system in accordance with another exemplary embodiment. Here, the beacons 401, 402, and 403 are placed in specific areas of indoor space, such as conference rooms, hallways, kitchens, offices, and other areas in a workspace, but the beacons are not associated with each of the rooms 404, 407, 413, and 414. Instead, information associated to a diagrammatic representation of the physical floor plan is provided to location database. A dataset containing strength and composition of the location signals from various beacons throughout the entire floor is created and overlaid on the diagrammatic representation of the physical floor plan. Thus, granular portions of the physical floor plan are associated to strength and composition of the location signals from various beacons to create several micro-locations. In this embodiment, individual beacons need not be moved regularly due to floor plan changes or in companies that have flexible, adaptable workspaces. When there is change in the physical floor plan, then a simple upload of the diagrammatic representation of the floor plan will be sufficient to recalibrate the program to adapt to the new floor plan and create new micro-locations. Using beacons as shown in FIG. 4 results in a dynamic map with virtual fenced micro-locations. In an embodiment, maps of physical resources, such as conference rooms, hallways, kitchens, offices, and other areas in a workspace, can also be mapped as micro-locations. At a given point, a mobile application on a user device may detect different location signals with certain signal strengths. This set of location signals and their associated signal strengths represents a data point that is unique to that physical position.

For example, as illustrated in FIG. 4, a limited dataset containing strength and composition of the location signals from the beacons 401, 402, and 403, and corresponding to the room 404 defines the micro-location 405. When a location-aware device 406 is outside the room 404, the receiver in the location-aware device 406 detects the location signals from the three beacons 401, 402, and 403. The device 406 communicates them along with a device identifier or a user identifier associated with the location-aware device 406 to the analytic server via an application program. The unique combination of strength and composition of the location signals from device 406 is used to determine that the device is within the micro-location 405.

As another example, when a location-aware device 411 is in the micro-location 412, then a receiver in the location-aware device 411 detects the location signals from the three beacons 401, 402, and 403. The device 411 communicates them along with a device identifier or a user identifier associated with the location-aware device 411 to the analytic server via an application program. The unique combination of strength and composition of the location signals from device 411 is used (by the analytic server) to determine that the device is within the micro-location 412.

Non-Limiting Example

A group of users request a health product from a health consumer protection company. Instead of requiring each user to provide rigorous personal information, the health consumer protection company monitors each user's activity by monitoring beacon signals received by each user's mobile/electronic device, generating a user activity profile for each user, and/or executing various artificial intelligence and rule-based analytical models.

The health consumer protection company may first place beacons throughout a common place visited by the users (e.g., office location). For instance, an office location of the users may be geo-fenced in a manner that identifies various locations (e.g., breakroom, bathroom, and kitchen). The beacon transmitters are configured to broadcast UUIDs identifying a location of the beacons and ultimately the geo-fenced area. Next, users may be asked to download an application operated by the analytics server. The application is configured to receive location signals broadcasted by the beacons. In some configurations, the application may be executing in the background and without obfuscating the mobile devices display or otherwise interfering with the operations of the mobile devices. The applications may be installed on the mobile devices (e.g., smart phones).

The analytics server may utilize different configurations to monitor users' locations. For instance, in some configurations, the users may be requested to wear (or otherwise carry) an electronic beacon transmitter. In some other configurations, a beacon receiver (configured to only receive beacon UUIDs and transmit the UUIDs to a server) may be carried by the users.

The analytics server may periodically send query instructions to the mobile applications installed on the mobile devices and may periodically identify the locations and travel paths associated with each user. For instance, the analytics server may periodically receive UUIDs from different mobile devices and may use the geo-fencing data to identify how many steps each user takes during a typical workday, how long each user spends at the breakroom; kitchen, bathroom, or other predetermined places during the day. The analytics server may then generate an activity profile for each user and store the above-described data. The analytics server may then execute various predetermined protocols/rules to identify an activity score for each user. The activity score may correspond to a quantified version of each user's activity level during a typical/average workday at his/her office.

In some configurations, the analytics server may also augment the activity profile using various other health-related data received from one or more biometric monitoring devices (e.g., heart rate monitor, smart watch, and pedometers). For instance, the analytics server may send an instruction to these biometric monitoring devices and record each user's biometric data accordingly.

Based on each user's respective score, the analytics server may recommend a product. For instance, when a user's score satisfies a score, the analytics server selects a product that matches the user's score. If the user's score does not satisfy the threshold (e.g., lower than a certain required score), the analytics server may then transmit a prompt to a computer (e.g., agent computer) that includes the user's activity profile and requests the agent to complete the user's request. The agent may then require more information before identifying a product for the user.

In some embodiments, the analytics server may also execute an artificial intelligence model to identify a suitable product for the user. The AI model may be trained (by the analytics server or any other third-party server) using historical data and previous users. When the AI model receives the score, the AI model may predict a suitable product for the user.

The foregoing method descriptions and the process flow diagrams are provided merely as illustrative examples and are not intended to require or imply that the steps of the various embodiments must be performed in the order presented. As will be appreciated by one of skill in the art the steps in the foregoing embodiments may be performed in any order. Words such as "then," "next," etc. are not intended to limit the order of the steps; these words are simply used to guide the reader through the description of the methods. Although process flow diagrams may describe the operations as a sequential process, many of the operations may be performed in parallel or concurrently. In addition, the order of the operations may be re-arranged. A process may correspond to a method, a function, a procedure, a subroutine, a subprogram, etc. When a process corresponds to a function, its termination may correspond to a return of the function to the calling function or the main function.

The various illustrative logical blocks, modules, circuits, and algorithm steps described in connection with the embodiments disclosed here may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the invention. Thus, the operation and behavior of the systems and methods were described without reference to the specific software code being understood that software and control hardware can be designed to implement the systems and methods based on the description here.

When implemented in software, the functions may be stored as one or more instructions or code on a non-transitory computer-readable or processor-readable storage medium. The steps of a method or algorithm disclosed here may be embodied in a processor-executable software module which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used here, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

When implemented in hardware, the functionality may be implemented within circuitry of a wireless signal processing circuit that may be suitable for use in a wireless receiver or mobile device. Such wireless signal processing circuit may include circuits for accomplishing the signal measuring and calculating steps described in the various embodiments.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

Any reference to claim elements in the singular, for example, using the articles "a," "an" or "the," is not to be construed as limiting the element to the singular.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

What is claimed is:

1. A method comprising:
periodically monitoring, by a server, location information of a plurality of users by periodically receiving, from an application executing on a mobile device of each user, location signals emitted by a plurality of beacons;
continuously updating, by the server, a user activity profile for each user containing a movement pattern representative of the user and based on the location information monitored via the plurality of beacons, a distance traveled within a predetermined time period, and a time spent at a pre-determined location;
generating, by the server, an activity score for each user based on the movement pattern in each user's activity profile;
executing, by the server, an artificial intelligence model to determine a health score associated with each user, the artificial intelligence model is trained based on historical activity data associated with a set of at least one of existing and past users, wherein the artificial intelligence model is configured to, upon receiving a user's activity score, determine an estimated health score of that user;
when the health score satisfies a threshold, determining, by the server using a predetermined pricing algorithm, a premium for each user that corresponds to each user's health score;
when the health score does not satisfy a threshold, routing the user's activity profile to an electronic device; and
upon receiving an updated health score for the user, dynamically updating, by the server, the artificial intelligence model based on the updated health score and the health score.

2. The method of claim 1, wherein the user activity profile comprises health attributes, habits, lifestyles, behaviors, and activities.

3. The method of claim 2, further comprising:
determining, by the server, the health attributes of the user by executing the artificial intelligence model based on the location information.

4. The method of claim 2, further comprising:
determining, by the server, behaviors by aggregating each user's location information at different timestamps.

5. The method of claim 1, further comprising:
determining, by the server, a mortality risk based on the user's activity profile.

6. The method of claim 1, further comprising:
iteratively training, by the server, the artificial intelligence model each time an erroneous health score is identified.

7. The method of claim 1, further comprising:
determining, by the server, micro-locations of each user by mapping the location information to a region of a predetermined space.

8. The method of claim 1, wherein the location information is in JavaScript Object Notation (JSON) format.

9. The method of claim 1, further comprising:
determining, by the server, the location information of each user based on a strength of the location signals emitted by the plurality of beacons.

10. A method comprising:
monitoring, by a server, location information of a plurality of users, using location signals received from a plurality of sensors, wherein each sensor of the plurality of sensors is configured to receive signals from a beacon within a plurality of beacons when the beacon is within a predetermined distance from the sensor, wherein the beacon is configured to attach to each user and constantly transmit a signal;
continuously generating, by the server, a user activity profile for each user containing a movement pattern representative of the user and based on the location information monitored via the plurality of beacons, a distance traveled within a predetermined time period, and a time spent at a pre-determined location;
generating, by the server, an activity score for each user based on the movement pattern in each user's activity profile;
executing, by the server, an artificial intelligence model to determine a health score associated with the user, the artificial intelligence model is trained based on historical data associated with a set of existing or past users, wherein the artificial intelligence model is configured to, upon receiving a user's activity score, determine an estimated health score of that user;
when the health score satisfies a threshold, determining, by the server using a predetermined pricing algorithm, a premium for each user based on each user's health score;
when the health score does not satisfy a threshold, routing the user's activity profile to an electronic device; and
upon receiving an updated health score for the user, dynamically updating, by the server, the artificial intelligence model based on the updated health score and the health score.

11. The method of claim 10, wherein the user activity profile comprises health attributes, habits, lifestyles, behaviors, and activities.

12. The method of claim 11, further comprising:
determining, by the server, the health attributes of the user by executing the artificial intelligence model based on the location information.

13. The method of claim 11, further comprising:
determining, by the server, behaviors by aggregating each user's location information at different timestamps.

14. The method of claim 10, further comprising:
determining, by the server, a mortality risk based on the user's activity profile.

15. The method of claim 10, further comprising:
determining, by the server, biometric parameters that are measured by collecting body fluid based on the location information.

16. The method of claim 10, further comprising:
determining, by the server, micro-locations of each user by mapping the location information to a region of a predetermined space.

17. The method of claim 10, wherein the location information is in JavaScript Object Notation (JSON) format.

18. A computer system comprising:
a plurality of beacons where each beacon is configured to broadcast location signals;
a plurality of mobile devices operated by a plurality of users where each mobile device is configured to receive location signals from at least one beacon;
a server in communication with at least the plurality of mobile devices, the server configured to:
periodically monitor location information of the plurality of users by periodically receiving, from an application executing on a mobile device of each user, location signals emitted by the plurality of beacons;
continuously update a user activity profile for each user containing a movement pattern representative of the user and based on the location information monitored via the plurality of beacons, a distance traveled within a predetermined time period, and a time spent at a pre-determined location;
generate an activity score for each user based on the movement pattern in each user's activity profile;
execute an artificial intelligence model to determine a health score associated with each user, the artificial intelligence model is trained based on historical activity data associated with a set of at least one of existing and past users, wherein the artificial intelligence model is configured to, upon receiving a user's activity score, determine an estimated health score of that user;
when the health score satisfies a threshold, determining, by the server using a predetermined pricing algorithm, a premium for each user that corresponds to each user's health score;
when the health score does not satisfy a threshold, routing the user's activity profile to an electronic device; and
upon receiving an updated health score for the user, dynamically update the artificial intelligence model based on the updated health score and the health score.

19. The computer system of claim 18, wherein the user activity profile comprises health attributes, habits, lifestyles, behaviors, and activities.

20. The computer system of claim 19, wherein the server is further configured to:
determine the health attributes of the user by executing the artificial intelligence model based on the location information.

* * * * *